United States Patent [19]
Lehmann et al.

[11] 3,999,422
[45] Dec. 28, 1976

[54] ULTRASONIC TEST METHOD AND APPARATUS FOR TESTING THICK-WALLED WORKPIECES

[75] Inventors: Kai Lehmann; Manfred Rehrmann, both of Efferen, Germany

[73] Assignee: Krautkramer-Branson, Incorporated, Stratford, Conn.

[22] Filed: May 8, 1975

[21] Appl. No.: 575,728

[30] Foreign Application Priority Data
May 17, 1974 Germany .......................... 2424075

[52] U.S. Cl. ............................. 73/67.8 S; 73/67.9
[51] Int. Cl.² ...................................... G01N 29/04
[58] Field of Search .......... 73/67.8 S, 67.9, 67.8 R, 73/67.7, 67.5 R, 71.5 US

[56] References Cited
UNITED STATES PATENTS

| | | | |
|---|---|---|---|
| 3,481,186 | 12/1969 | Cellitti et al. .................. | 73/67.9 |
| 3,485,087 | 12/1969 | Brech ............................. | 73/67.9 |
| 3,805,597 | 4/1974 | Ohta et al. ..................... | 73/67.9 |
| 3,872,715 | 3/1975 | Pittaro ........................... | 73/67.9 |

*Primary Examiner*—James J. Gill
*Assistant Examiner*—Stephen A. Kreitman
*Attorney, Agent, or Firm*—Ervin B. Steinberg; Philip J. Feig

[57] ABSTRACT

The invention concerns an apparatus and method for ultrasonically testing thick-walled workpieces at an increased scanning speed by the use of a plurality of ultrasonic test probes wherein the probes are selectively rendered operable. The transmit probes are temporarily inhibited from transmitting search signals into the workpiece for a time interval during which the receipt of a defect responsive echo signal by a receive transducer is anticipated. The scan frequency is determined therefore by a clock circuit and the transmission of search signals is halted only temporarily for a brief period during which time there is no skipping in the predetermined transmitting sequence of the transducer probes.

12 Claims, 1 Drawing Figure

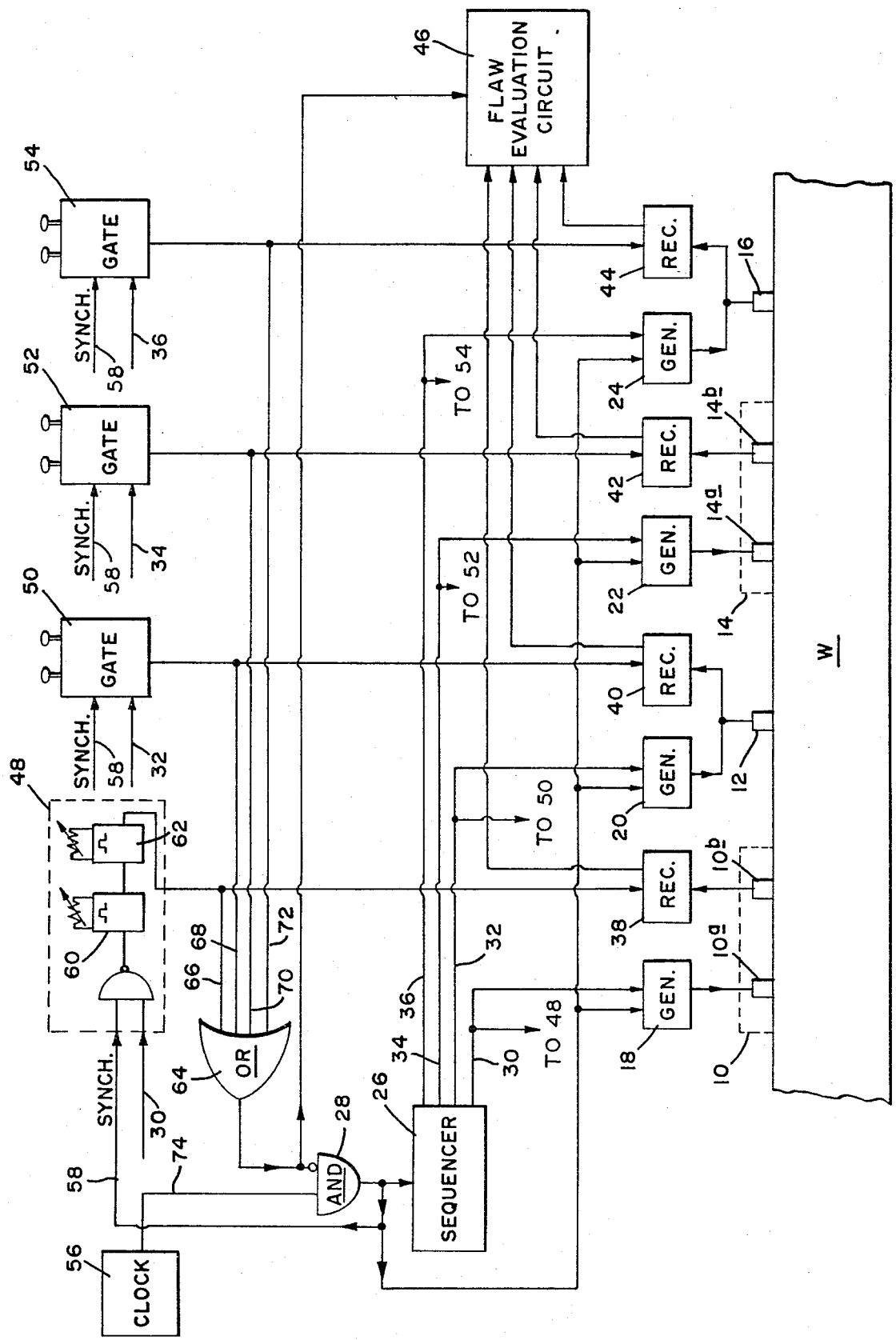

ULTRASONIC TEST METHOD AND APPARATUS FOR TESTING THICK-WALLED WORKPIECES

SUMMARY OF THE INVENTION

This invention concerns an apparatus and method for ultrasonically testing thick walled specimens, such as the walls of nuclear reactor vessels, with increased scanning speed by the use of a plurality of ultrasonic test probes wherein the probes are rendered operable in time sequence.

In the nondestructive testing of workpieces with ultrasonic energy test probes are coupled to the metallic wall of a test object by a suitable coupling medium, such as water or oil. The transmit probes include by means of a suitable support a piezoelectric element, e.g. quartz or barium titanate, adapted to be subjected to vibrations responsive to high frequency energy supplied to the electrode layer of the element from the high frequency pulse generator portion of the ultrasonic apparatus via a suitable cable. The receive transducers, suitably spaced from the transmit transducers, include a similar piezoelectric element which receives an ultrasonic echo signal arising from a portion of the transmitted signal being reflected at a defect. The latter element is then excited by such acoustic energy and provides an electrical pulse signal at an ultrasonic frequency, such signal being fed to the receiver amplifier of an ultrasonic test apparatus. Transmit and receive transducers can be constructed also to form a single probe acoustically insulated from one another by a suitable layer of barrier material. Furthermore, when operating a plurality of probes it is known to operate combinations of several parallel coupled test probes. Moreover, it is known for detecting defects which are disposed normal to the workpiece surface to use angle test probes which transmit a search signal at an angle to the workpiece surface. Still further, when using electronic logic circuits for evaluating echo amplitude and transit time, it is known to use accept/reject signals or signal monitors which automatically indicate the receipt of an echo signal by an electrical signal as soon as the echo signal occurs within a predetermined range of the gate or, as the case may be, when a predetermined amplitude is exceeded. By using a plurality of monitors the gates of which overlap, several predetermined zones in the workpiece can be monitored.

When testing thick walled specimens special problems arise due to the increased wall thickness which causes a longer transit time of the ultrasonic signals in the material under test. The increased transit times decrease the test speed of the usual test methods. The transit time is dependent upon the propagation speed of the ultrasonic energy and upon the thickness of the material, i.e. the path travelled by the pulse signal. In order to test the entire thickness of a specimen it is known to dispose a plurality of probes in a side-by-side arrangement so that search signals are transmitted from each probe or probe combination. To accomplish this, a specific probe is energized, the respective search beam enters the workpiece and after a predetermined lapse of time, if a defect is present, a defect responsive echo signal is received by a respective receive probe and such signal is then displayed and/or evaluated. In accordance with the known method a new search pulse is transmitted only when the time interval, subject to calculation, between the transmittal of the search pulse and the (possible) receipt of a defect responsive echo signal has elapsed. In view of the fact that each search pulse can be utilized to test only a limited predetermined region of the workpiece, the switching circuit must take into account the respective time interval, thereby causing the scanning speed of the probes to be limited.

The present invention addresses itself to the problem of significantly increasing the scanning speed in a multi-probe system without loss of defect indications. A simple increase of the scanning speed is precluded by the following difficulties. For increasing the scanning rate another, respectively a second, transmit probe must be excited and its search pulse transmitted into the workpiece prior to the receipt of the echo signal which is associated with the previously excited transmit probe (associated with another test zone). Particularly, when a large quantity of probes is used the danger exists that a transmit transducer transmits a pulse when the return of an echo pulse from the test region is expected so that the transmit pulse is mistakenly identified as an indication of a defect.

In order to avoid these difficulties when using a significantly higher scan frequency, the transmit pulses are temporarily inhibited at the locations where the receipt of a defect responsive echo signal arising from one or more previously transmitted search pulses is anticipated. The gate circuits associated with respective probes are adjusted for providing an output signal corresponding to the predetermined test zones in the workpiece and this output signal is utilized for temporarily inhibiting the transmission of further search signals.

As a result, when using a plurality of probes, an increased scanning speed is achieved without superimposed transmit signals being identified as defect responsive echo signals. Hence, a higher test speed for thick walled workpieces, such as nuclear reactors, is obtained.

A principal object of the present invention, therefore, is the provision of a method and apparatus for testing thick walled workpieces at a higher repetition rate by temporarily inhibiting the ultrasonic probes from transmitting search pulses at certain signal conditions.

Another object of this invention is the provision of means for temporarily inhibiting the operation of ultrasonic transmit probes without disturbing the sequence in which these probes are normally energized.

A further object of the invention is the provision of means for inhibiting the operation of transmit probes during a time interval corresponding to the anticipated receipt of a defect responsive echo signal by any probe forming a part of a probe array.

Further and still other objects of the present invention will become apparent when the specification is read in conjunction with the accompanying drawing.

BRIEF DESCRIPTION OF THE DRAWING

The FIGURE is a schematic electrical block diagram of a preferred embodiment of the invention.

DETAILED DESCRIPTION OF THE INVENTION

Referring to the FIGURE, a plurality of ultrasonic transducer probes 10, 12, 14 and 16 are shown coupled to the entrant surface of a workpiece W by a suitable couplant, such as oil or water. The probes in the array comprise transmit transducers 10a and 14a for transmitting ultrasonic energy search signals into the workpiece and receive transducers 10b and 14b for receiving ultrasonic energy echo signals reflected from an acoustic discontinuity, i.e. a defect, in the workpiece W. In the alternative, the probes can be combined transmit-receive probes 12 and 16, the construction of which is well known in the art. Each transmit transducer in the array is associated with a respective pulse generator 18, 20, 22 and 24 for sequentially transmitting an ultrasonic search signal into the workpiece responsive to a signal from sequencer 26.

The sequencer 26, in a preferred embodiment, comprises a shift register or a ring counter. The sequencer, responsive to the receipt of a pulse signal from an AND circuit 28 causes a signal to be manifest along only one of the output conductors 30, 32, 34 and 36 which are connected to the respective pulse generators 18, 20, 22 and 24. For example, upon receipt of a first pulse from AND gate 28, a signal is conducted from the sequencer 26 along conductor 30 to pulse generator 18 for causing the transmit transducer 10a to transmit an ultrasonic search signal into the workpiece W. Upon receipt by the sequencer 26 of a second pulse from AND circuit 28, a signal is conducted along conductor 32 to the pulse generator 20 for causing the probe 12 to transmit an ultrasonic search signal into the workpiece W. Subsequently, probes 14a and 16 are energized in timed sequence. The manner by which AND circuit 28 transmits pulses to sequencer 26 will be explained below.

A portion of the ultrasonic search signal upon intercepting an acoustic discontinuity, such as a defect in the workpiece, is reflected back toward the entrant surface of the workpiece whereat the signal is received by the respective receive transducer of the probe. Thus, when transmit transducer 10a transmits a search signal into the workpiece, a defect causes a reflected signal to be received by receive transducer 10b. The received echo signal is coupled to an associated receiver circuit 38, 40, 42 and 44, there being one receiver circuit coupled to each probe adapted to receive echo signals. The output of each receiver circuit is coupled to a flaw evaluation circuit 46 the construction of which is known in the art.

In the present invention each respective receiver circuit is activated during a predetermined time interval for receiving defect responsive echo signals originating from a predetermined test zone in the workpiece. Each of the gate circuits 48, 50, 52 and 54 provides a signal to an associated receiver circuit 38, 40, 42 and 44 for permitting echo signals received only during predetermined respective time intervals corresponding to the test zones to be transmitted through the associated receiver circuit to the flaw evaluation circuit 46.

The construction of the gate circuit is best seen with reference to gate circuit 48. Upon the simultaneous receipt of a pulse from the sequencer 26 along conductor 30 and a system synchronization pulse from AND circuit 28 along conductor 58 a first adjustable monostable multivibrator 60 is actuated. The pulse width of the output of this monostable multivibrator 60 is adjusted by a knob to provide a predetermined delay before actuating a second adjustable monostable multivibrator 62. The pulse width of the output of the monostable multivibrator 62 is adjusted by a second knob to correspond to a time interval during which the receipt of a defect responsive echo signal is anticipated. Therefore, the open gate time interval determines the zone from which a defect responsive echo signal is passed from the associated receiver to the flaw evaluation circuit 46 and is adjustable with respect to starting time measured from the main bang and with respect to duration of the interval. During the following sequence gate 50 is operated responsive to the receipt of a pulse from the AND circuit 28, conductor 58, and a signal along conductor 32 from the sequencer 26. Thus, the gates are operated in predetermined timed sequence synchronized with the probes.

The output signal from a respective gate circuit 48, 50, 52 and 54 indicative of an open gate condition is conducted to a respective input of an OR circuit 64 in addition to being conducted to an associated receiver circuit 38, 40, 42 and 44. When a signal is manifest at any one of the input conductors 66, 68, 70 or 72 of the OR circuit 64, a signal at the output of the OR circuit 64 is conducted to the flaw evaluation circuit 46 for activating this circuit and to an inverting input of AND circuit 28. The resulting output signal from the OR circuit 64 acting upon the AND gate 28 inhibits the sequencer 26 from causing a probe to transmit a search signal into the workpiece during the time interval during which a defect responsive echo signal to be evaluated can be expected by the receive transducers. In the absence of a signal at the output of OR circuit 64, that is, an echo responsive signal is not anticipated at the receive transducers, and responsive to the receipt of a clock pulse along conductor 74, a pulse is transmitted from AND circuit 28 to the sequencer 26 for causing a respective probe 10, 12, 14 or 16 of the array to sequentially transmit a search signal into the workpiece W. When an output is present at OR circuit 64, the AND circuit 28 is inhibited and thus no pulses are received by sequencer 26, hence the sequencer is temporarily held at its present position, but will resume sequencing the pulse generators in response to the inhibit signal being removed and the arrival of the clock pulse.

The output pulse signal from AND circuit 28 is electrically connected to each of the gate circuits and each of the pulse generators for synchronizing the timing of the test system. Since the input stage of each gate circuit and pulse generator includes a NAND circuit, a synchronizing signal must be manifest at the input of these circuits for actuating the respective circuits.

It will be apparent that the logic circuits, that is AND circuit 28 and OR circuit 64, cause the sequencer 26 to be inhibited for a time interval corresponding to the time interval during which a defect responsive echo signal arising from a defect in a predetermined zone in the workpiece can be expected to be received by any one of the receive transducers. If all gates are closed, the sequencer 26 sequentially energizes the pulse generators at a rate corresponding to the frequency of the pulses from clock 56.

It will be apparent to those skilled in the art that the above described pulse-echo ultrasonic test apparatus allows the testing of a workpiece W at a higher frequency than prior systems. In prior systems, the frequency is limited by the time required for a search pulse to travel from the entrant surface of a workpiece to the rear wall whereat the signal is reflected back toward the entrant surface. In the present system, the frequency is determined by a clock 56 operating at a pulse repetition rate for causing a plurality of sequentially initiated search pulses, each pulse transmitted by a respective sequentially operated transducer probe, to concurrently be in transit through the workpiece and the sending of a search signal is stopped only temporarily for a brief time interval corresponding to the time when a defect responsive echo signal can be expected from a predetermined zone in the workpiece. Importantly it should be noted that there is no skipping in the predetermined transmitting sequence of the transducer probes, but only a temporary pause.

What is claimed is:

1. The method of testing a workpiece by the ultrasonic pulse-echo test technique comprising:
   acoustically coupling a plurality of transducer test probes to the surface of a workpiece;
   energizing said probes in predetermined time sequence with an electrical signal for causing said probes responsive to being energized to transmit an ultrasonic search pulse into the workpiece for causing a plurality of sequentially initiated search pulses to concurrently traverse the workpiece, and
   inhibiting temporarily the progress of said sequence and the energizing of said probes during the time interval in which the receipt of an echo signal arising from an acoustic discontinuity being intercepted by a respective search pulse is to be sensed by one of said probes forming said plurality.

2. The method of testing as set forth in claim 1, and resuming said predetermined time sequence after the lapse of said interval.

3. The method of testing as set forth in claim 2, said time interval being adjustable.

4. The method of testing as set forth in claim 3, said time interval being adjustable as to its starting time and duration.

5. The method of testing as set forth in claim 1, each of said test probes including a transmit transducer and a receive transducer.

6. The method of testing as set forth in claim 1, each of said probes being associated with a respective time interval responsive to being energized.

7. The method of testing as set forth in claim 1, said time interval being less than the time span required for an ultrasonic search pulse transmitted to traverse the distance from a test probe to the acoustic discontinuity presented by the rear wall of the workpiece and the resultant echo being sensed by one of said probes.

8. A pulse-echo ultrasonic test apparatus comprising:
   transducer probe means adapted to be energized for transmitting an ultrasonic search pulse into a workpiece and for subsequently receiving an echo signal responsive to an acoustic discontinuity in the workpiece;
   pulse sequencing means coupled to said probe means for energizing said probe means sequentially at a predetermined rate for causing a plurality of sequentially initiated search pulses to concurrently traverse the workpiece;
   gate means coupled to said probe means for establishing a time interval within which a discontinuity responsive echo signal subsequent to the transmission of a respective search pulse and received by said probe means is to be conducted to an evaluation circuit, and
   inhibit means coupled to said gate means and said pulse sequencing means for inhibiting temporarily operation of said sequencing means and energization of said probe means during said time interval.

9. A pulse-echo ultrasonic test apparatus comprising:
   a plurality of transducer probe means adapted to be coupled to a workpiece;
   pulse sequencing means coupled to said plurality of probe means for causing said transducer probe means to be energized in predetermined timed sequence and for causing each probe means responsive to being energized to transmit an ultrasonic search pulse into the workpiece for further causing a plurality of sequentially initiated search pulses to concurrently traverse the workpiece and subsequently receive an echo signal arising from an acoustic discontinuity intercepted by the search pulse;
   gate means coupled to each of said probe means for establishing a time interval within which an echo signal received by a respective probe means is conducted to an evaluation circuit, and
   inhibit means coupled to said gate means and said pulse sequencing means for inhibiting temporarily operation of said sequencing means to prevent energization of said probe means during the existence of said time interval.

10. A pulse-echo ultrasonic test apparatus as set forth in claim 9, and means for actuating said inhibiting means responsive to a respective gate means having started said time interval.

11. A pulse-echo ultrasonic test apparatus as set forth in claim 9, said pulse sequencing means comprising a pulse generating means and a switching means, and said inhibiting means comprising logic means for preventing operation of said pulse sequencing means.

12. A pulse-echo ultrasonic test apparatus comprising:
   a plurality of transducer probe means adapted to be coupled to the surface of a workpiece;
   a plurality of receiver circuits, one associated with each of said probe means, coupled to said probe means for providing an acoustic discontinuity responsive echo signal received by a respective probe means to an evaluation circuit;
   a clock providing a sequence of signals;
   sequencing means operated responsive to the signals from said clock;
   a plurality of gate circuits, one for each of said probe means, coupled to said sequencing means and said receiver circuits for causing each of said gate circuits to be rendered open in predetermined sequence for an adjustable respective time interval and during such time interval causing an echo signal received by an associated probe means to be conducted via the respective receiver circuit to said evaluation circuit;
   means coupling said sequencing means to said clock and to said probe means for energizing said probe means responsive to said clock signals in said predetermined sequence for causing each probe means to sequentially transmit a search pulse into the workpiece for causing a plurality of sequentially initiated search pulses to concurrently traverse the workpiece and receive an echo signal responsive to an acoustic discontinuity in the workpiece, and
   inhibit means coupled serially between said sequencing means and said gate circuits for inhibiting temporarily operation of said sequencing means during the existence of a said respective time interval.

* * * * *